(12) United States Patent
Kraus

(10) Patent No.: US 8,182,535 B2
(45) Date of Patent: May 22, 2012

(54) HEIGHT-ADJUSTABLE SPINAL IMPLANT

(76) Inventor: Kilian Kraus, Werneck (DE)

( * ) Notice: Subject to any disclaimer, the term of this patent is extended or adjusted under 35 U.S.C. 154(b) by 499 days.

(21) Appl. No.: 12/261,118

(22) Filed: Oct. 30, 2008

(65) Prior Publication Data

US 2009/0112320 A1    Apr. 30, 2009

(30) Foreign Application Priority Data

Oct. 30, 2007  (DE) .......................... 10 2007 052 042

(51) Int. Cl.
*A61F 2/44* (2006.01)
(52) U.S. Cl. ..................... 623/17.15; 623/17.11; 606/61; 606/246
(58) Field of Classification Search ............... 623/17.11, 623/17.15, 17.16; 606/247, 61, 246
See application file for complete search history.

(56) References Cited

U.S. PATENT DOCUMENTS

| | | | | |
|---|---|---|---|---|
| 6,019,793 | A | * | 2/2000 | Perren et al. ................ 623/17.16 |
| 7,575,601 | B2 | * | 8/2009 | Dickson ...................... 623/17.15 |
| 2002/0082695 | A1 | * | 6/2002 | Neumann .................... 623/17.11 |
| 2002/0161441 | A1 | * | 10/2002 | Lang et al. .................. 623/17.11 |
| 2003/0045877 | A1 | | 3/2003 | Yeh |
| 2004/0019353 | A1 | * | 1/2004 | Freid et al. ...................... 606/69 |
| 2004/0162618 | A1 | | 8/2004 | Mujwid et al. |
| 2004/0172129 | A1 | * | 9/2004 | Schafer et al. ............. 623/17.11 |
| 2005/0216000 | A1 | * | 9/2005 | Colleran et al. ................ 606/61 |
| 2005/0285398 | A1 | * | 12/2005 | Sivley ........................... 285/334 |
| 2006/0058877 | A1 | * | 3/2006 | Gutlin et al. ............... 623/17.11 |
| 2006/0241762 | A1 | | 10/2006 | Kraus |
| 2010/0292794 | A1 | * | 11/2010 | Metz-Stavenhagen .... 623/17.11 |

FOREIGN PATENT DOCUMENTS

| | | |
|---|---|---|
| WO | 2004052245 A1 | 6/2004 |
| WO | 2005/055887 A2 | 6/2005 |
| WO | WO 2005/055887 A2 * | 6/2005 |

* cited by examiner

*Primary Examiner* — Thomas C. Barrett
*Assistant Examiner* — Samuel Hanna
(74) *Attorney, Agent, or Firm* — Laurence A. Greenberg; Werner H. Stemer; Ralph E. Locher

(57) ABSTRACT

A height-adjustable spinal implant has first and second components that are rotationally fixed relative to one another and axially movable along a central longitudinal axis of the implant. Each of the components have at least two wall segments that are fixed on a base and that extend in the direction of the central longitudinal axis and are at a radial distance from the latter. Circumferentially adjacent wall segments each flank a space in which a wall segment of the respective other component extends and is axially guided. A drive element is disposed in the interior of the implant that engages with the second component in a meshing relationship. The drive element bears, in the load direction, on the first component and has a toothed ring that is used for its rotary actuation. For the rotary actuation of the drive element, an access opening is present in a wall segment of the first component. The free ends of the wall segments of the first component are connected to each other by a holding element.

18 Claims, 6 Drawing Sheets

HEIGHT-ADJUSTABLE SPINAL IMPLANT

CROSS-REFERENCE TO RELATED APPLICATION

This application claims the priority, under 35 U.S.C. §119, of German application DE 10 2007 052 042.7, filed Oct. 30, 2007; the prior application is herewith incorporated by reference in its entirety.

BACKGROUND OF THE INVENTION

Field of the Invention

The invention relates to a height-adjustable spinal implant for insertion between vertebral bodies. The implant includes first and second components, which are displaceable relative to each other in the manner of a telescope along a central longitudinal axis of the implant. The components are axially movable but are held on each other in a manner secure against rotation relative to each other. Each of the components comprises at least two wall segments that are fixed on a base and that extend both in the direction of the central longitudinal axis and also in a circumferential direction. The wall segments are at a radial distance from the central longitudinal axis. Wall segments adjacent in the circumferential direction each flank a space in which a wall segment of the respective other component extends and is axially guided. In an interior enclosed by the first and second components, there is a drive element which is held on the first component and by means of which the second component can be moved relative to the first component in the axial direction.

A height-adjustable spinal implant of the foregoing kind is described, for example, in my earlier application US 2006/0241762 A1 and its counterpart international PCT publication WO 2005/055887 A2.

Such a spinal implant has a drive element with a radially encircling groove. At the free ends of the wall segments of the first component, there are projections which engage radially into this groove and by which the drive element is held. However, when high mechanical loads are placed on the spinal implant, there is a danger of the drive element being forced out of its fixture as a consequence of a bending of the wall segments or of the projections.

SUMMARY OF THE INVENTION

It is accordingly an object of the invention to provide a spinal implant, which overcomes the above-mentioned disadvantages of the heretofore-known devices and methods of this general type and which provides for a height-adjustable spinal implant that has an improved mechanical load-bearing capacity.

With the foregoing and other objects in view there is provided, in accordance with the invention, a height-adjustable spinal implant, comprising: first and second components rotatably fixed relative to one another and axially
  movable along a central longitudinal axis of the spinal implant;
  each of said first and second components having at least two wall segments fixed on a base and extending in a direction of said central longitudinal axis at a radial spacing distance therefrom and forming an interior of the implant;
  with two circumferentially adjacent wall segments each flanking a space in which a wall segment of the respectively other component extends and is axially guided;
  a drive element with the following features:
    disposed in said interior of the implant enclosed by said wall segments;
    engaging said second component in a screw mechanism relationship;
    having a toothed ring arranged coaxially with respect to said central longitudinal axis and used for rotary actuation thereof; and
    bearing on said first component in a load direction;
  a wall segment of said first component and said toothed ring being formed with an access opening extending therethrough for rotary actuation of said drive element by way of a maneuvering tool; and
  a holding element in said interior connecting free ends of said wall segments of said first component to one another.

In other words, the height-adjustable spinal implant according to the invention has first and second components which are held in a manner secure against rotation relative to each other and are axially movable along a central longitudinal axis of the implant. The first and second components each have at least two wall segments that are fixed on a base and that extend, on the one hand, in the direction of the central longitudinal axis and, on the other hand, in the circumferential direction of the implant, at a radial distance from the central longitudinal axis. Adjacent wall segments flank a space in which a respective wall segment of the other component extends and is axially guided. The height-adjustable spinal implant also has a drive element, which is arranged in an interior of the implant enclosed by the wall segments. The second component engages with the drive element in the manner of a screw mechanism.

A screw mechanism in this context is to be understood as a mechanical gear in which a spindle and a drive nut cooperate. The spindle, driven by the drive nut, can be moved in its longitudinal direction. As far as the term screw mechanism is concerned, it is irrelevant in this context whether the spindle has an inner thread and the driving nut an outer thread, or whether the spindle has an outer thread and the driving nut an inner thread. Therefore, the drive element, which cooperates with the second component in the manner of a screw mechanism, can have an outer thread and also an inner thread.

Moreover, according to the invention, the drive element has a toothed ring arranged coaxially with respect to the central longitudinal axis of the spinal implant and used for the rotary actuation of the drive element. The drive element bears, in the load direction, on the first component. A wall segment of the first component is breached by an access opening via which the toothed ring for the rotary actuation of the drive element is accessible with the aid of a maneuvering tool. A holding element, which connects the free ends of the wall segments of the first component to each other, is present in the interior of the spinal implant.

If such a spinal implant according to the invention is exposed to a high axial load, i.e. subjected to a force that presses the first and second components together, then high mechanical loading occurs at the location where the drive element is connected to the first component. The free ends of the wall segments of the first component are advantageously stabilized by the holding element arranged in the interior of the implant. In particular, a spreading force acting on the wall segments in the radial direction can be absorbed. The load-bearing capacity of the implant can be increased significantly.

Advantageous developments of the spinal implant according to the invention are set out in the dependent claims discussed below. The spinal implant according to the invention can advantageously be combined with the features of one or more dependent claims.

According to one embodiment of the spinal implant, the holding element and the first component are designed in one piece. This measure permits a reduction in the number of components for the spinal implant, which has advantages in terms of production engineering. Moreover, the load-bearing capacity of the spinal implant can be increased by the one-part construction.

According to another advantageous embodiment, the drive element is fixed on the holding element so as to rotate about the central longitudinal axis, and the drive element preferably bears, in the load direction, on a support surface extending at right angles to the central longitudinal axis of the holding element. In an advantageous embodiment of this kind, the holding element performs a dual function. On the one hand, the wall segments are stabilized by the holding element, and, on the other hand, the holding element gives the drive element a stable support surface.

According to an advantageous development, the drive element can bear with the toothed ring on the support surface. The contact surface between the toothed ring and the support surface can be made small such that only minimal friction occurs between these components. For example, the toothed ring can stand with the tips of its teeth on the support surface. It is particularly advantageous that the risk of injury to surrounding tissue can be reduced by the fact that the toothed ring is in contact with the support surface. At least from this direction, the penetration of tissue into the screw mechanism can be prevented by the support surface. Such protection of the screw mechanism against tissue possibly penetrating into the toothed ring from the direction of the support surface is particularly advantageous, since the interior of the spinal implant is usually filled with bone chips or a bone substitute material.

According to another embodiment of the spinal implant, a further improvement to the protection of the surrounding tissue is achieved by the fact that the toothed ring is designed in the manner of a crown wheel of a crown gear, and the holding element has a recess that breaches the support surface and that communicates with an access opening. According to this embodiment, the crown wheel is driven particularly advantageously from the direction of the support surface. In such a spinal implant, the entry of tissue into the area of the screw mechanism can be largely avoided by the toothed ring resting on the support surface. Moreover, the crown wheel is driven with the aid of a maneuvering tool which gains access to the crown wheel by way of the access opening in the wall segment. Tissue bearing on the implant in the area of the wall segments can be kept substantially away from the screw mechanism, since it is only in the area of the access opening that there is the possibility of tissue coming into contact with the screw mechanism. However, the access opening is largely covered by the maneuvering tool. Thus, the risk of injury to the surrounding tissue can be reduced in this area too.

The access opening is introduced into the wall segment preferably in the area of the holding element. An access opening may possibly represent a weakening of the wall segment in question. If the access opening is advantageously introduced into the associated wall segment in the area of the holding element, then this access opening is located in a mechanically stable area of the spinal implant. The mechanical weakening of the spinal implant by the access opening can thus be minimized.

According to another embodiment, the holding element has a through-opening in which there engages a fixing element. One end of the fixing element is connected to the drive element, while the other end has an engage-behind element that engages behind the holding element on the side thereof directed away from the drive element. As a result, the drive element is mechanically connected to the holding element both in the load direction and also counter to the load direction. The spinal implant can therefore be subjected to both compression and also tensile loading, which extends its range of use. The holding element and the fixing element can be screwed together, for example, for their mechanical connection.

According to one embodiment, the drive element is designed such that it has an outer thread that meshes with an inner thread of the second component. Such cooperation between the drive element and the second component represents a particularly simple screw mechanism that can be mechanically loaded. Particularly advantageously, the inner thread can be formed in the inner faces of the wall segments of the second component.

According to another embodiment, the outer thread is arranged on that end of the drive element directed toward the second component. The drive element is thus advantageously exposed only to compression loads and not to tensile loads.

According to another embodiment, the drive element is arranged on the first sleeve part in such a way that the outer thread, seen in the axial direction, is situated outside the first sleeve part. By means of such an arrangement of the drive element on the first sleeve part, the second sleeve part can be moved particularly far relative to the first sleeve part. Moreover, the position of the drive element allows the outer radius of the outer thread to be chosen such that it protrudes into the area of the wall thickness of the second component. An inner thread can thus be cut particularly advantageously into the inside wall of the second component.

To improve its maneuverability, the spinal implant can be connected to a maneuvering tool. It is possible in particular, with the aid of the maneuvering tool, to position the spinal implant exactly in a desired position during a medical intervention. To allow the spinal implant to be received by a maneuvering tool, the wall segment with the access opening has at least one engage-behind element used for radial fixing, i.e. for fixing of the spinal implant relative to the maneuvering tool in a radial direction with respect to the central longitudinal axis of the implant. According to an advantageous development of the engage-behind element, the latter has an engage-behind surface facing in the direction of the interior of the implant. An engage-behind surface oriented in this way permits simple and effective reception of the implant, with radial fixing, by the maneuvering tool.

According to another embodiment, which also on its own represents a solution to the object of the invention, the spinal implant has the following features:

The height-adjustable spinal implant according to the invention has first and second components which are held in a manner secure against rotation relative to each other and are axially movable along the central longitudinal axis of the implant. The first and second components each have at least two wall segments that are fixed on a base and that extend, on the one hand, in the direction of the central longitudinal axis and, on the other hand, in the circumferential direction of the implant, at a radial distance from the central longitudinal axis. Adjacent wall segments flank a space in which a respective wall segment of the other component extends and is axially guided. The height-adjustable spinal implant also has a drive element, which is arranged in an interior of the implant enclosed by the wall segments. The second component engages with the drive element in the manner of a screw mechanism. The drive element comprises a toothed ring arranged coaxially with respect to the central longitudinal axis of the spinal implant and used for the rotary actuation of the drive element. The drive element bears, in the load direction, on the first component. A wall segment of the first component is breached by an access opening via which the toothed ring for the rotary actuation of the drive element is accessible with the aid of a maneuvering tool. The wall segments of the first and second components are connected to each other with a form-fit engagement acting in the radial direction.

Such an embodiment, both on its own and also in combination with one of the preceding embodiments, represents an advantageous solution to the object of the invention.

When the spinal implant is subjected to a high load, in particular to a load in the axial direction, a spreading force acts especially on the second component. Therefore, in order to improve the stability of the spinal implant, the first and second components can be held on each other by a form-fit engagement acting in the radially outward direction.

According to another embodiment, in order to produce a form-fit engagement acting in the radial direction, the narrow sides of the wall segments facing each other in the circumferential direction are designed, at least along part of their length, such that they engage in each other with a form fit. A form-fit engagement between the wall segments of the first and second components is particularly advantageous, since the wall segments extend in an axial direction of the spinal implant and therefore permit simple guiding in the axial direction with simultaneous stabilization in the radial direction.

According to an advantageous development, the wall segments, on their narrow sides, are each provided with a tab projecting in the circumferential direction. The tabs of the second component engage behind those of the first component. The aforementioned embodiment is a particularly simple solution for a radially acting form-fit engagement.

According to another embodiment, as an alternative to a radially outwardly acting form-fit engagement between the wall segments of the first and second components, the drive element and the wall segments of the second component can cooperate in the manner of a radially outwardly acting form-fit engagement. Accordingly, the outer thread of the drive element and the inner thread of the second component have, seen in a radial direction, flanks that are inclined with respect to the central longitudinal axis of the implant. The supporting flanks of the outer thread of the drive element face toward the second component and are beveled, and they enclose, together with the central longitudinal axis, an acute angle open toward the second component. The counterflanks of the inner thread of the second component cooperate with the aforementioned flanks of the drive part and have a complementary shape. Special types of threads designed in this way are also referred to as compression threads or negative threads. When a force acts in the axial direction of the implant, the second component is thus pressed in the direction of the drive element, and the corresponding supporting flanks of the second component and of the drive element thus cooperate in such a way that the wall segments of the second component experience an inwardly directed moment of force. Upon loading of the implant, the wall segments of the second component are thus drawn inward in the direction of the central longitudinal axis. This moment counteracts an outwardly directed spreading moment of the wall segments. The mechanical load-bearing capacity of the implant can be increased significantly in this way.

According to one embodiment, the inner thread of the second component and the outer thread of the drive element have a dovetail-shaped configuration, seen in a plane containing the central longitudinal axis. Such a configuration of the intermeshing threads can further improve their guiding and also the mechanical stability of the spinal implant. Moreover, for compression loads and also tensile loads, a dovetail-shaped thread of this kind offers the effect of a compression thread.

According to one embodiment, a spinal implant for replacing a damaged vertebral body is inserted between adjacent vertebral bodies using support plates provided at its ends. By virtue of their specific design, these support plates not only allow the implant to be connected to the adjacent vertebral bodies in a manner secure against slipping, they also make it possible to flexibly adjust the angle between the surfaces of the adjacent vertebral bodies and the central longitudinal axis of the implant. Particularly advantageously, according to one embodiment, at least part of the spinal implant is made of a material based on stainless steel, titanium or a polyether ketone (PEEK). These materials are medically well proven, have a high load-bearing capacity and are therefore particularly suitable for the construction of spinal implants.

Other features which are considered as characteristic for the invention are set forth in the appended claims.

Although the invention is illustrated and described herein as embodied in a height-adjustable spinal implant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
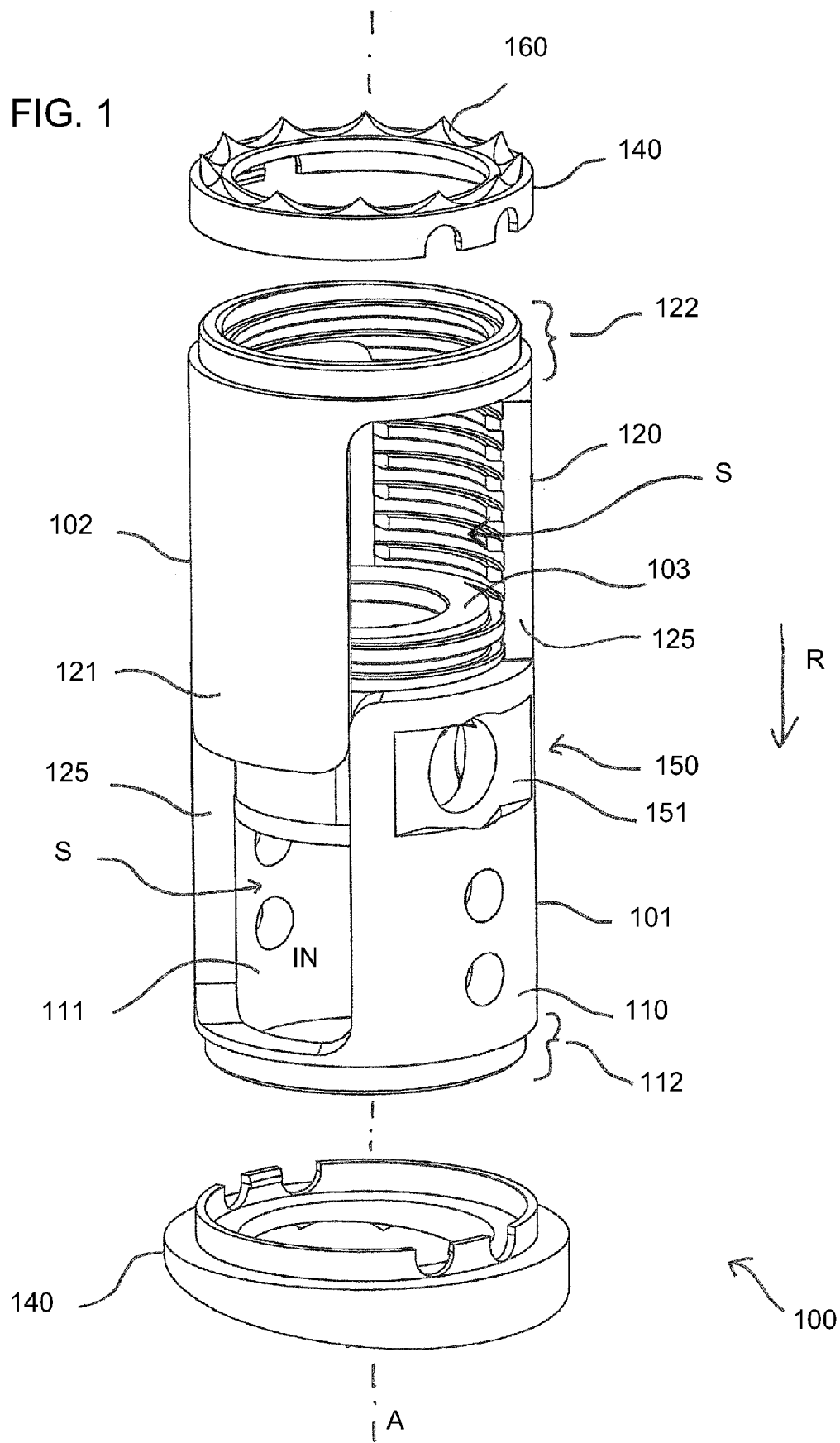
FIG. 1 is a partly exploded perspective view of a spinal implant according to the invention.

Referring now to the figures of the drawing in detail and first, particularly, to FIG. 1 thereof, the apparatus according to the invention is a spinal implant 100 with first component 101 and a second component 102 which are oriented coaxially with respect to a central longitudinal axis A. The first and second components 101, 102 each have wall segments 110, 111, 120, 121 connected to one another in the area of a base 112, 122. The wall segments 110, 111, 120, 121 each flank a space S, seen in the circumferential direction of the implant 100. The wall segments 110, 111 of the first component 101 engage in the corresponding spaces S between the wall segments 120, 121 of the second component 102. Conversely, the wall segments 120, 121 of the second component 102 engage in the spaces S present between the wall segments 110, 111 of the first component 101. The first and second components 101, 102 are displaceable relative to each other in the manner of a telescope in the axial direction, that is to say along the central longitudinal axis A, but in the radial direction are held on each other in a manner secure against rotation. The wall segments 110, 111, 120, 121 of the first and second components 101, 102, like the segments of a cylinder jacket surface, are at a radial distance from the central longitudinal axis A and extend both in the circumferential direction and also in the axial direction of the implant 100. In the circumferential direction, the wall segments 110, 111, 120, 121 have narrow sides 125 facing toward each other. The respective narrow sides 125 of the first and second components 101, 102 slide on each other during axial movement of the components 101, 102. Seen in the circumferential direction, the narrow sides 125 of the wall segments 110, 111, 120, 121 bear on each other and in this way lock the first and second components 101, 102 in a manner secure against rotation relative to each other.

Support plates 140 can be connected to the spinal implant 100 at the ends of the first and second components 101, 102, in the area of the respective bases 112, 122. These support plates 140 promote the anatomically correct fit of the spinal implant 100 and its anchoring between the healthy vertebral bodies. For anatomical adaptation of the spinal implant 100, it is possible, as can be seen from the lower support plate 140 shown in FIG. 1, for the angle between the surface of the support plate 140 in contact with the adjacent healthy vertebral body and the central longitudinal axis A of the spinal implant 100 to deviate from the perpendicular. To facilitate the fusion of the spinal implant 100 with the surrounding tissue, and to ensure that the spinal implant 100 is held secure against slipping between the healthy vertebral bodies, the support plates 140 can be provided with spikes or projections 160.

During a surgical intervention, it is necessary to adjust the length or height of the spinal implant 100 and to position it exactly between the adjacent vertebral bodies. The height or length of the spinal implant 100 is adjusted by displacing the first and second components 101, 102 relative to each other in the manner of a telescope. To displace the first and second components 101, 102 relative to each other, a drive element 103 is located in an interior IN enclosed by the components 101, 102. The interior IN is the volume which, in the radial direction to the central longitudinal axis A of the spinal implant 100, is delimited by the wall segments 110, 111, 120, 121 of the first and second components 101, 102. In the axial direction, the interior IN is delimited by the respective bases 112, 122 of the first and second components 101, 102. The interior IN is accessible from the ends of the spinal implant 100 and extends over the full length thereof. Bone material of the adjacent vertebral bodies can grow into the spinal implant 100 such that, over the course of time, the vertebral bodies fuse with each other by way of the interior IN.

The spinal implant 100 is exposed mainly to compression loads. The drive element 103, cooperating with the second component 102 in the manner of a screw mechanism, is therefore supported in load direction R on the first component 101. For rotary actuation of the drive element 103, a maneuvering tool (not shown) can reach the drive element 103 by way of the access opening 150. The maneuvering tool can additionally be used for the exact positioning of the spinal implant 100. For this purpose, the maneuvering tool can engage in a flattened part 151 present on the outside of one wall segment 110 of the first component 101.

Figure 3:
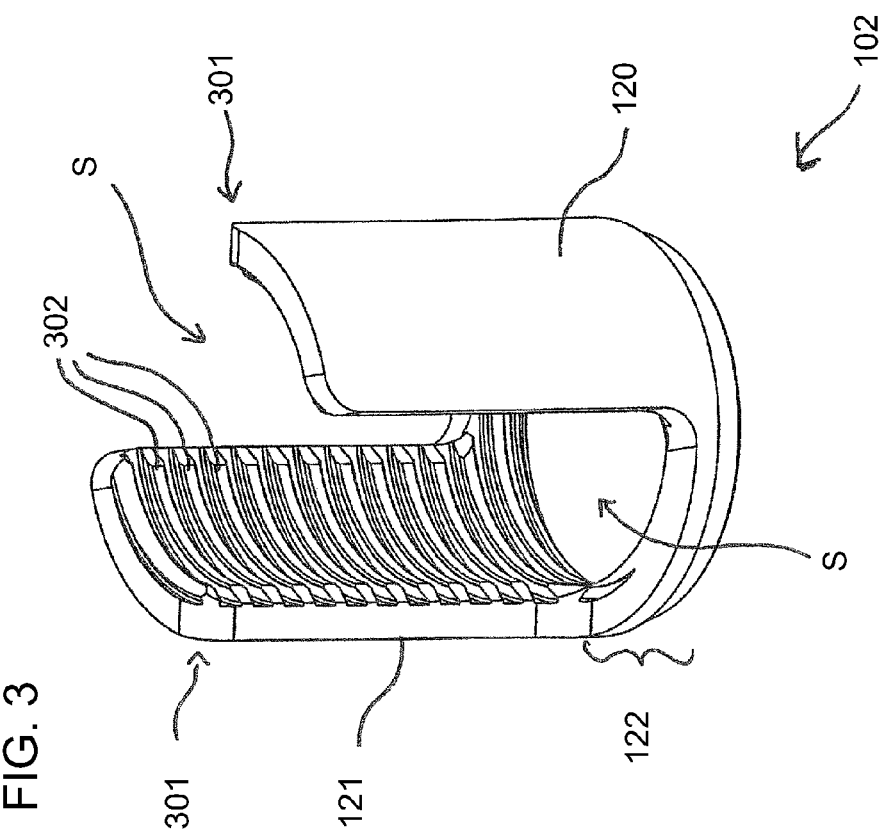
FIG. 3 is a reverse perspective view of a second component thereof.

For the explanations below, reference is made not only to FIG. 1 but also to FIG. 2 to 4, in which the first component 101, the second component 102 and the drive element 103 are each shown individually in perspective views.

Figure 4:
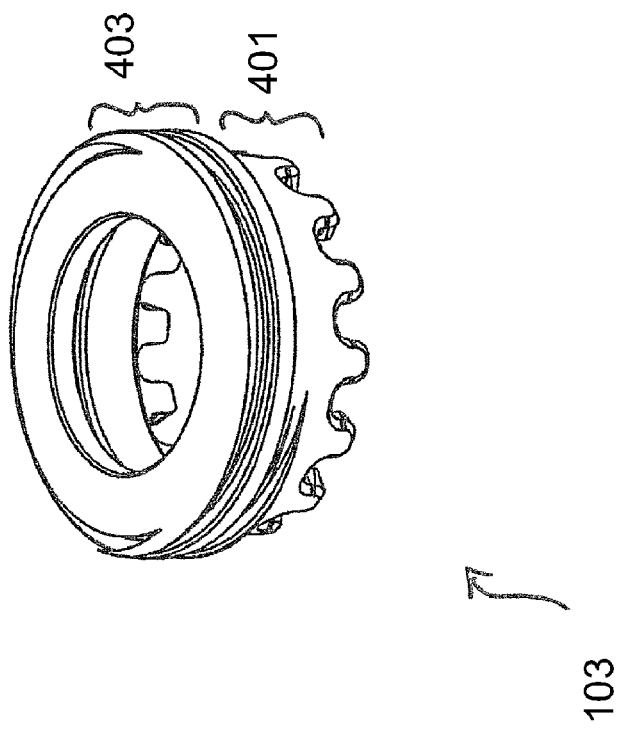
FIG. 4 is a perspective view of a drive element.

FIG. 4 shows an illustrative embodiment of the drive element 103. On its side directed toward the first component 101, the drive element 103 has a toothed ring 401 which, in order to drive the drive element 103, engages with a pinion (not shown) in the manner of a crown gear. On its radial outer surface, the drive element 103 has an outer thread 403, which cooperates with an inner thread 302 (cf. FIG. 3) present on the inner face of the wall segments 120, 121 of the second component 102.

Figure 2:
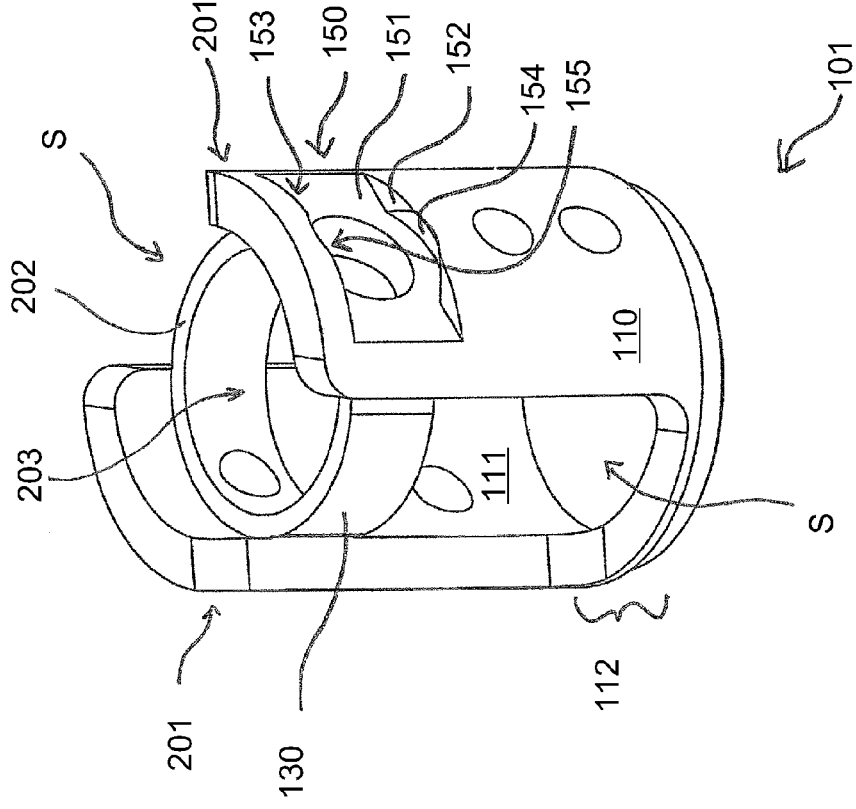
FIG. 2 is a perspective view of a first component of the spinal implant.

In load direction R, the drive element 103 bears with the tips of the teeth of the toothed ring 401 on a support surface 202 of a holding element 130 (cf. FIG. 2). Consequently, the drive element 103 has only a small area of contact with the support surface 202.

The first and second components 101, 102 of the spinal implant 100 are moved relative to each other, in the manner of a telescope, with the aid of the drive element 103. In doing this, the outer thread 403 of the drive element 103 meshes with the inner thread 302 of the second component 102. By means of a rotation of the drive element 103 about the central longitudinal axis A, the second component 102 is driven by the drive element 103 in the manner of a screw mechanism (cf. FIG. 1).

The drive element 103 can be driven by a pinion (not shown) which cooperates with the toothed ring 401 on the underside of the drive element 103. The pinion driving the drive element 103 is preferably rotatable about another axis oriented radially with respect to the central longitudinal axis A and is guided through a shaft. Such a drive pinion can be brought into the area of the toothed ring 401 of the drive element 103 by way of the access opening 150 (cf. FIG. 2). A wall segment 110 of the first component 101 has the access opening 150 for this purpose.

FIG. 2 shows a perspective view of the first component 101. The free ends 201 of the wall segments 110, 111 of the first component are connected by a preferably annular holding element 130, which can in particular be designed in one piece with the first component 101. The drive element 103 shown in FIG. 4 sits with its toothed ring 401 on the support surface 202 directed upward in FIG. 2. The support surface 202 is also preferably oriented at right angles to the central longitudinal axis A.

For the rotary actuation of the drive element 103 with said pinion, the maneuvering tool engages on the toothed ring 401 of the drive element 103 by way of the access opening 150 present in the wall segment 110 of the first component 101. The pinion meshing with the toothed ring 401, in order to drive the drive element 103, is guided through a shaft and located on the tip of a maneuvering tool (not shown). To permit access of the pinion to the toothed ring 401, the support surface 202 has a recess. The support surface 202 extending in a ring shape in the radial direction is therefore interrupted in the area of the access opening 150, such that, in the orientation of the first component 101 shown in FIG. 2, a pinion of the maneuvering tool inserted through the access opening 150 can access the drive element 103 or its toothed ring 401 from underneath. The pinion of the maneuvering tool and the toothed ring 401 of the drive element preferably cooperate here in the manner of a crown gear.

During a surgical intervention, it is necessary to adjust the length or height of the spinal implant 100 and also to position it exactly between the adjacent healthy vertebral bodies. The height or length of the spinal implant 100 is adjusted by telescopically displacing the first and second components 101, 102 relative to each other with the aid of the drive described above. To permit the exact positioning of the spinal implant 100, it is connected to a maneuvering tool. In this context, it should be noted that the connection between the spinal implant 100 and a maneuvering tool is to be rotationally fixed and secure, but should also be releasable without difficulty, in particular without the aid of further tools. The wall segment 110 with the access opening 150 therefore has engage-behind elements 154, 155 (cf. FIG. 2) that serve for the radial fixing of the maneuvering tool. The engage-behind elements 154, 155 are let into the boundary surfaces 152, 153 extending perpendicular to the central longitudinal axis A. A maneuvering tool, which engages in the flattened part 151, can thus lock the spinal implant 100 in the axial direction of the maneuvering tool by means of the surfaces of the engage-behind elements 154, 155 that face in the direction of the interior IN of the implant 100. To lock the spinal implant 100 in a rotationally fixed manner relative to the longitudinal axis of the maneuvering tool, corresponding jaws of the maneuvering tool can engage with the boundary surfaces 152, 153. The axial direction of the maneuvering tool is substantially perpendicular, that is to say oriented radially with respect to the central longitudinal axis A of the spinal implant 100.

For the telescopic adjustment of the height of the spinal implant 100, the drive element 103 has an outer thread 403 at that end directed toward the second component 102. When the spinal implant 100 is subjected to a compression load, which is transmitted to the drive element 103 or its outer thread 403 by way of the inner thread 302 of the second component 102, only compression forces acting on the drive element 103 are forwarded to the support surface 202 of the holding element 130. The drive element 103 is preferably arranged such that the outer thread 403 protrudes above the surfaces visible in FIG. 2 at the upper end of the free ends 201 of the first component 101. The outer thread 403 of the drive element 103 thus extends, as seen in the radial direction, beyond the inner wall of the wall segments 110, 111 of the first component 101. In this way, it is easily possible for the outer thread 403 of the drive element 103 to mesh with an inner thread that is let directly into the wall segments 120, 121 of the second component 102. Moreover, such an arrangement of the outer thread 403 of the drive element 103 permits a particularly long course of travel of the first and second components 101, 102 relative to each other.

Figure 5:
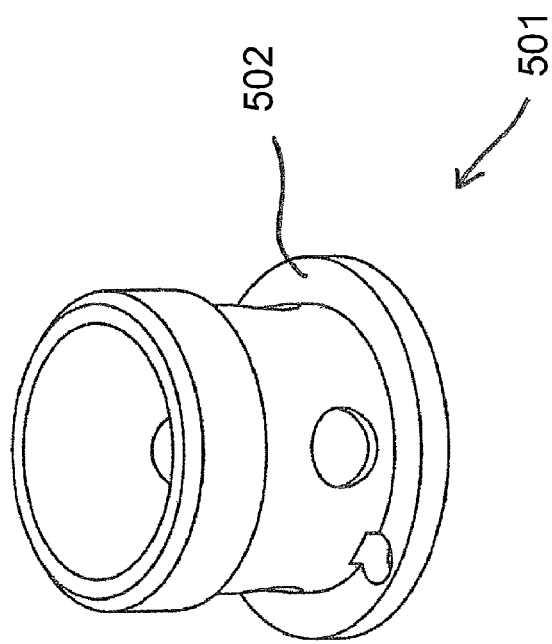
FIG. 5 is a perspective view of a fixing element.

The support surface 202 of the holding element 103, in the component 101 shown in FIG. 2, has a through-opening 203 at its center. This through-opening 203 is traversed by a fixing element 501, which is shown in a perspective view in FIG. 5. The fixing element 501 is fixed to the drive element 103 by means of a screwed connection, for example. The engage-behind element 502 present at the lower end of the fixing element 501 shown in FIG. 5 engages behind the holding element 130 on that side directed away from the second component 102. The drive element 103 and the fixing element 501 thus form a common component having a groove 601 (cf. FIG. 6) in which the holding element 130 comes to lie.

Figure 6:
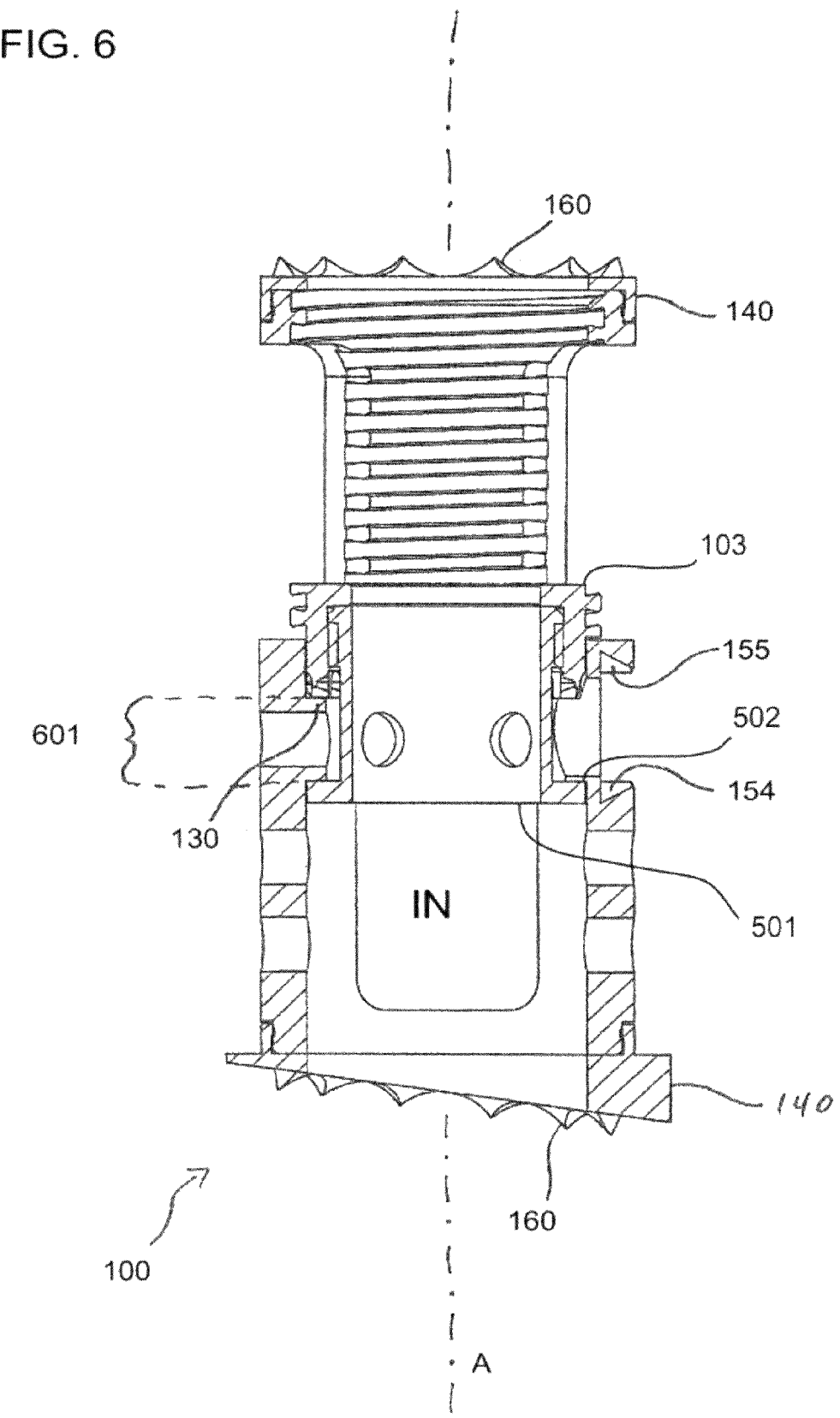
FIG. 6 shows a longitudinal section through the spinal implant.

FIG. 6 shows a longitudinal section through the spinal implant 100. The surfaces of the engage-behind element 154, 155 directed toward the interior IN can be clearly seen, as also can the support plates 140 present at the ends of the spinal implant 100. The support plates 140 can have inclined surfaces for adapting the position of the spinal implant 100 between the adjacent vertebral bodies. For example, the surface of the support plate 140 at the lower part of the spinal implant shown in FIG. 6 is not oriented perpendicularly with respect to the central longitudinal axis A. To ensure that the spinal implant 100 is locked between adjacent vertebral bodies in a manner secure against slipping, spikes 160 can be present at the ends of the support plates 140. The figure also shows clearly the interior IN that extends along the entire length of the spinal implant 100 and that is accessible from the ends of the implant 100, i.e. in the area of the support plates 140.

According to an alternative illustrative embodiment, the spinal implant 100 does not have a holding element 130 for stabilizing the free ends 201 of the first component 101 (cf. FIG. 2).

A spreading moment of the wall segments 110, 111, 120, 121, which occurs when the spinal implant 100 is subjected to a compression load, is absorbed by virtue of the fact that the first and second components 101, 102 are connected to each other with a form-fit engagement acting in the radial direction. A radial form-fit engagement can be produced, by way of the drive element 103, between the free ends 301 of the second component 102. Alternatively, the wall segments 120, 121 of the second component 102 can enter into a radially acting form-fit engagement with the wall segments 110, 111 of the first component 101.

A radially acting form-fit engagement of this kind between the first and second components 101, 102, or between the second component 102 and the drive element 103, represents on its own a solution for stabilizing the spinal implant 100, although it can also be used in combination with a holding element 130.

Figure 7:
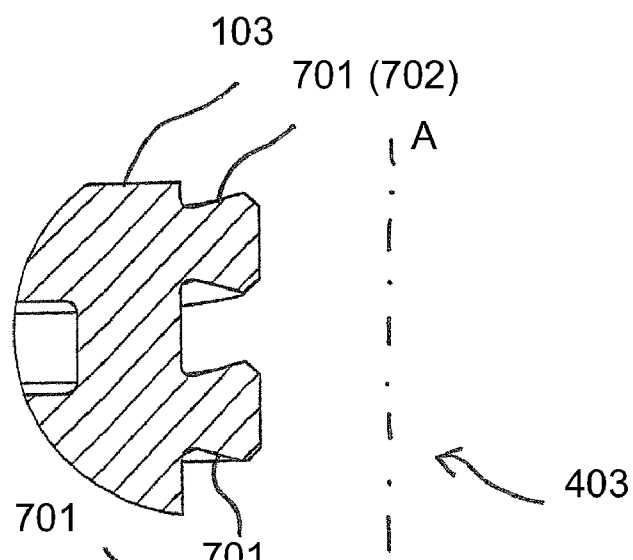
FIG. 7 to FIG. 9 show detailed views in the area of the drive element.
Figure 8:
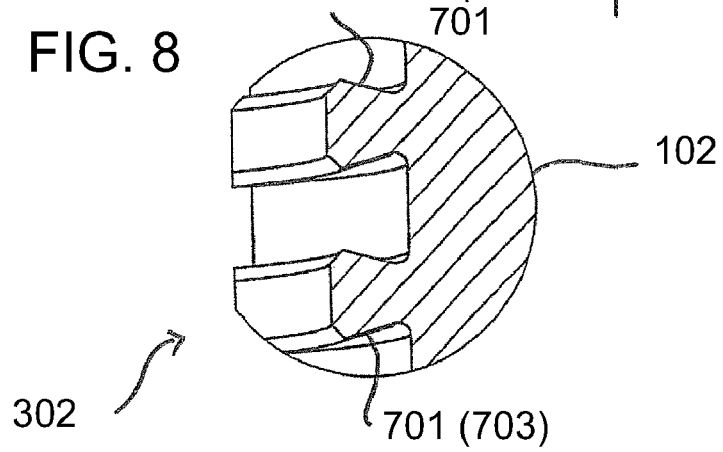
Figure 9:
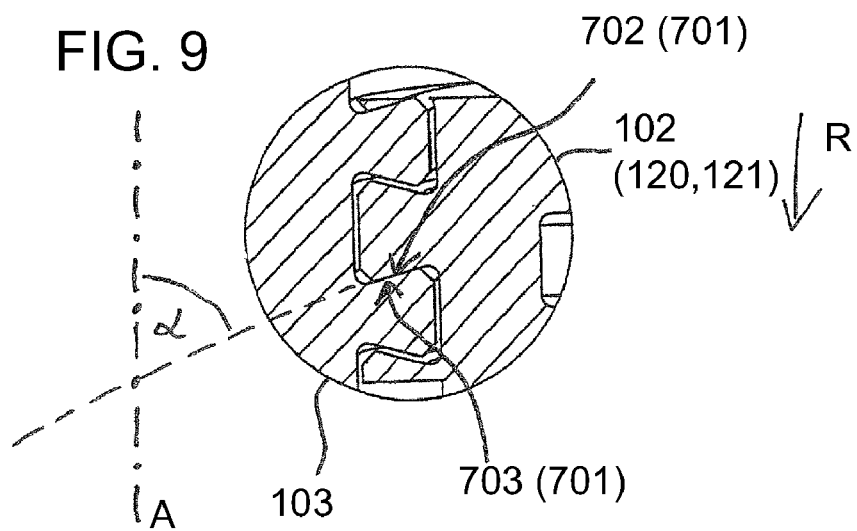

According to the illustrative embodiments in FIG. 7 to 9, the drive element 103 has an outer thread 403 with a dovetail-shaped cross section.

The second component 102 has an inner thread 302 of complementary shape, which is likewise dovetail-shaped. The dovetail-shaped outer thread 403 of the drive element 103 and the inner thread 302 of the second component 102 have flanks 701 that are inclined with respect to the central longitudinal axis A. To produce a form-fit engagement which acts in the radial direction and which, upon loading of the spinal implant 100, counteracts a spreading moment of the free ends 301 of the wall segments 120, 121 of the second component 102, it is important that the supporting flanks 702 of the drive element 103 and the corresponding supporting counterflanks 703 of the second component 102 are inclined with respect to the central longitudinal axis A. Thus, as is shown in FIG. 9, the supporting flank 702 of the drive element 103 encloses, with the central longitudinal axis A, an acute angle α open in the direction of the second component 102. The counterflank 703 of the second component 102, cooperating with the supporting flank 702 of the drive element 103, has a complementary shape. When a force acts on the second component 102 in the load direction R, the inclined flanks 701 mean that the corresponding wall segment 120, 121 of the second component 102 will experience a moment of force oriented in the direction of the central longitudinal axis A. This moment of force counteracts a spreading moment acting on the wall segments 120, 121 of the second component 102.

Figure 10:
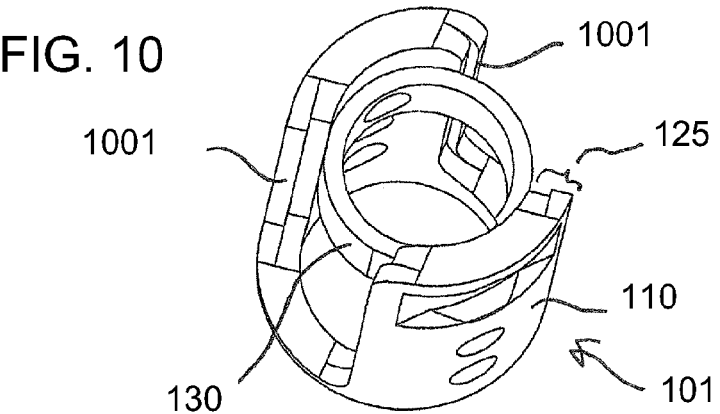
FIGS. 10 and 11 are perspective views and FIG. 12 is a cross-sectional view of details of the wall segments of the first and second components.
Figure 11:
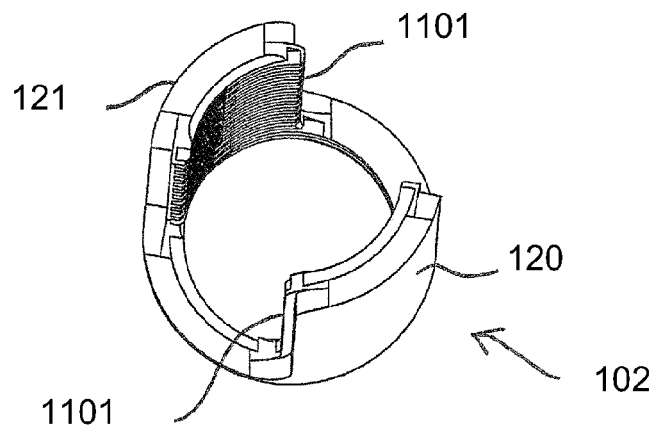
Figure 12:
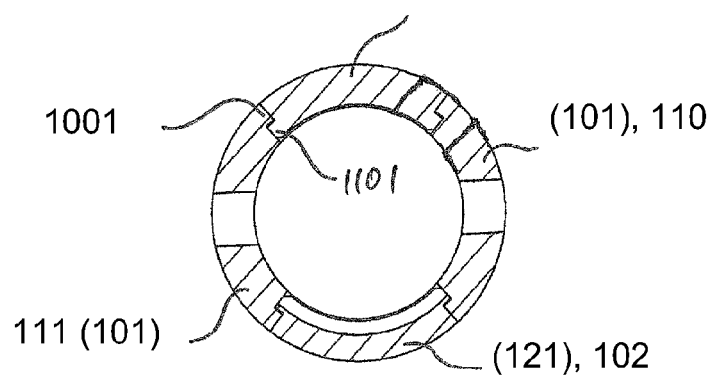

According to another illustrative embodiment, in an alternative or possibly in addition to a dovetail-shaped configuration of the outer thread 403 of the drive element 103 and of the inner thread 302 of the second component 102, the radially acting form-fit engagement between the wall segments 110, 111 of the first component 101 and the wall segments 120, 121 of the second component 102 is ensured by tabs 1001, 1101 present on their narrow sides 125, as shown in FIG. 10 to 12. FIG. 10 shows a perspective view of the first component 101. The first component 101 has, on its narrow sides 125, tabs 1001 projecting in the circumferential direction. The second component 102, shown in FIG. 11, has tabs 1101 of complementary shape in the area of its wall segments 120, 121. As the cross-sectional view in FIG. 12 shows, the tabs 1101 of the second component 102 engage, as seen in the radial direction, behind the tabs 1001 of the first component 101. A spreading moment acting on the wall segments 120, 121 of the second component 102 can be transferred, by way of the tabs 1101, 1001, to the wall segments 110, 111 of the first component 101. Seen in the axial direction, the tabs 1001, 1101 preferably extend along the full length of the narrow sides 125 of the wall segments 110, 111, 120, 121. The first component 101 shown in FIG. 10, like the component 101 shown in FIG. 2, has a holding element 130, which performs the functions already described. In particular, a spreading moment, which originates from the second component 102 (cf. FIG. 11), more precisely from the wall segments 120, 121 thereof, and which is transferred to the wall segments 110, 111 of the first component 101 via the tabs 1001, 1101 present on the first and second components 101, 102, is absorbed by the holding element 130.

A particularly preferred material for a medical implant is a material based on titanium, stainless steel, or a polyether ketone (PEEK). Such materials are not generally rejected by body tissue, and they form a good union with the latter. Moreover, the aforementioned materials have a high degree of strength. To improve its strength, the PEEK material can be reinforced with carbon fibers (CF-PEEK).

The invention claimed is:

1. A height-adjustable spinal implant, comprising:
   a) first and second components rotatably fixed relative to one another and axially movable along a central longitudinal axis of the spinal implant;
      each of said first and second components having at least two wall segments fixed on a base and extending in a direction of said central longitudinal axis at a radial spacing distance therefrom and forming an interior of the implant;
      with two circumferentially adjacent wall segments each flanking a space in which a wall segment of the respectively other component extends and is axially guided;
   b) a drive element:
      disposed in said interior of the implant enclosed by said wall segments;
      engaging said second component in a screw mechanism relationship;
      having a toothed ring arranged coaxially with respect to said central longitudinal axis and used for rotary actuation thereof; and
      bearing on said first component in a load direction;
   c) a wall segment of said first component being formed with an access opening extending therethrough for rotary actuation of said drive element via said toothed ring by way of a maneuvering tool; and
   d) a holding element in said interior connecting free ends of said wall segments of said first component to one another, said drive element being fixed on said holding element for rotation about said central longitudinal axis and bearing, in the load direction, on a support surface extending at right angles to said central longitudinal axis.

2. The spinal implant according to claim 1, wherein said holding element and said first component are formed in one piece.

3. The spinal implant according to claim 1, wherein said drive element bears with said toothed ring on said support surface.

4. The spinal implant according to claim 1, wherein said toothed ring is configured as a crown wheel of a crown gear, and said holding element is formed with a recess breaching said support surface and communicating with said access opening.

5. The spinal implant according to claim 1, wherein said holding element has a through-opening formed therein and a fixing element engages in said through-opening, and said fixing element has one end connected to said drive element and another end with an engage-behind element configured to engage behind said holding element on a side thereof directed away from said drive element.

6. The spinal implant according to claim 1, wherein said drive element is formed with an outer thread configured to mesh with an inner thread of said second component.

7. The spinal implant according to claim 6, wherein said inner thread is formed in inner faces of said wall segments of said second component.

8. The spinal implant according to claim 6, wherein said outer thread is formed on an end of said drive element directed toward said second component.

9. The spinal implant according to claim 6, wherein said drive element is disposed on said first sleeve part such that said outer thread, seen in the axial direction, is situated outside said first sleeve part.

10. The spinal implant according to claim 1, which comprises at least one engage-behind element, for radially fixing a maneuvering tool, disposed on said wall segment having said access opening formed therein.

11. The spinal implant according to claim 10, wherein said at least one engage-behind element has an engage-behind surface facing in a direction of said interior.

12. The spinal implant according to claim 1, wherein said wall segments of said first and second components are connected to one another in a form-fitting engagement relationship acting in a radial direction.

13. The spinal implant according to claim 12, wherein said wall segments have narrow sides facing each other in a circumferential direction and engaging one another with a form fit along at least a part of a length thereof.

14. The spinal implant according to claim 13, wherein each of said narrow sides of said wall segments have a tab projecting in the circumferential direction, and said tabs of said second component engaging behind said tabs of said first component.

15. The spinal implant according to claim 6, wherein:
   supporting flanks of said outer thread of said drive element face toward said second component and, seen in the radial direction, are inclined relative to said central longitudinal axis of the implant and enclose an acute angle with said central longitudinal axis, open toward said second component; and
   counterflanks of said inner thread of said second component cooperate with said supporting flanks and have a complementary shape.

16. The spinal implant according to claim 15, wherein said outer thread of said drive element and said inner thread of said second component have a dovetail-shaped configuration, seen in a sectional plane containing said central longitudinal axis.

17. The spinal implant according to claim 1, which comprises a support plate on an end of the respective said component intended to bear on a vertebral body.

18. The spinal implant according to claim 1, wherein at least parts of the spinal implant are made of a material based on a material selected from the group consisting of stainless steel, titanium, and polyether ketone.

* * * * *